US000001978H

(19) United States

(12) Statutory Invention Registration

Freiburger et al.

(10) Reg. No.: US H1978 H

(43) Published: Aug. 7, 2001

(54) MONOLITHIC FILMS HAVING ZONED BREATHABILITY

(75) Inventors: Sarah Jane Marie Freiburger, Kaukauna; David Arthur Fell, Neenah, both of WI (US)

(73) Assignee: Kimberly-Clark Worldwide, Inc., Neenah, WI (US)

(21) Appl. No.: 09/312,429

(22) Filed: May 14, 1999

(51) Int. Cl.[7] ..... B32B 5/18

(52) U.S. Cl. ..... 156/78

*Primary Examiner*—Charles T. Jordan
*Assistant Examiner*—Aileen J. Baker
(74) *Attorney, Agent, or Firm*—Kimberly Clark Worldwide, Inc.

(57) ABSTRACT

Monolithic films are provided having controlled regional breathability with high WVTR regions and low WVTR regions. The zoned monolithic films are be made by selectively applying adhesive to the monolithic film.

22 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MONOLITHIC FILMS HAVING ZONED BREATHABILITY

FIELD OF THE INVENTION

The present invention relates to monolithic films. More particularly, the present invention relates to monolithic films having zoned breathability and methods of making the same.

BACKGROUND OF THE INVENTION

Various types of garments are presently available for absorbing human discharge. Examples of these garments include baby diapers, feminine care products, incontinence garments and the like. Generally speaking, the basic structure of this class of garments requires an aqueous liquid pervious body-side liner, an absorbent pad containing one or more layers for receiving and absorbing the discharge, and an aqueous liquid impervious backing member for containing the discharge. Such garments usually include a film material that serves as an aqueous liquid impervious outer cover. However, such film material lacks breathability, causing the absorbent garments to be hot and uncomfortable.

Monolithic films are "breathable" barriers in the sense that the film acts as a barrier to aqueous liquids and particulate matter but allows water vapor and air to pass therethrough. By achieving and maintaining high breathability, it is possible to provide an article that is more comfortable to wear since the migration of water vapor through the fabric helps reduce and/or limit discomfort resulting from excess moisture trapped against the skin. Thus, such an article can potentially contribute to an overall improved skin wellness.

Accordingly, breathable films have become an important article of commerce, finding a wide variety of applications. For example, breathable films have been used as outer covers for personal care products such as diapers, training pants, incontinence garments, feminine hygiene products and the like. In addition, breathable films have likewise found use in protective apparel and infection control products such as surgical gowns, surgical drapes, protective workwear, wound dressings and bandages. Often breathable films are utilized as a multilayer laminate. The films can provide the desired barrier properties to the article while other materials laminated thereto can provide additional characteristics such as strength, abrasion resistance and/or softness and drapability. For example, fibrous webs such as nonwoven fabrics allow the laminate to retain its breathability and can provide additional strength as well as an article having a cloth-like feel. Thus, breathable film laminates can be used in a variety of applications including, for example, those described above.

In addition, monolithic films that act as a barrier to bacteria and viruses can provide an article or garment that reduces the contamination of the surroundings and the spread of infections and illness caused by the bacteria and viruses.

Although the breathability provided by breathable films and/or laminates thereof is advantageous in many articles, there exist some situations where high breathability can be undesirable. For example, in absorbent personal care articles such as diapers or incontinence garments designed to absorb and contain aqueous liquid human exudates the breathable barrier and absorbent core generally work together to retain bodily fluids discharged into the garment. However, when fluid (aqueous liquid) is retained within the absorbent core significantly higher amounts of water vapor begin to pass through the breathable barrier. The increased amounts of water vapor passing through the outer cover can form condensate on the outer portion of the garment. The condensate is simply water but can be perceived by the wearer as leakage. In addition, the condensate can create a damp uncomfortable feel to the outer portion of the garment which is unpleasant for those handling the article.

It is believed that the skin wellness and/or improved comfort benefits of breathable outer covers are not achieved at areas directly adjacent the portion of the absorbent core retaining considerable amounts of aqueous liquid (e.g. typically those areas of the central or crotch region of the garment). Providing a breathable barrier which has less or limited breathability in such regions, while providing good breathability in the remaining regions, would provide a garment with excellent wearer comfort yet which limits the potential for outer cover dampness. Thus, a breathable barrier that provides either zoned or controlled regional breathability is highly desirable.

Therefore, there exists a need for a breathable film having regions with varied levels of breathability. In addition, there exists a need for such films which retain the desired barrier properties and which are capable of lamination to additional materials. Further, there exists a need for methods of making such films and in particular methods of reliably obtaining the desired levels of breathability in distinct regions of a film.

Thus, it becomes apparent that a need exists for an absorbent undergarment, diaper training pants or the like, that exhibits desired absorbency and containment characteristics of absorbent garments, such as undergarments, while improving comfort during use.

SUMMARY OF THE INVENTION

The aforesaid needs are fulfilled and the problems experienced by those skilled in the art overcome by the monolithic films of the present invention which, in one aspect, comprises a first breathable region having a thickness less than 100$\mu$ and a WVTR of at least 800 g/m$^2$/24 hours and a second region having a WVTR (also referred to as porosity) less than that of the first region wherein the WVTR of the second region is at least 15% less than the WVTR of the first region. The film has a hydrohead of at least about 50 mbar. The second region desirably has minimum dimensions of 5 cm by 5 cm and still more desirably comprises from about 5% to about 75% of the area of said film. In a further aspect, the first region can have a WVTR in excess of about 2500 g/m$^2$/24 hours and the second region a WVTR less than about 1500 g/m$^2$/24 hours.

Additionally and/or alternatively, the second region can have a WVTR at least about 50% less than the WVTR of the first region. Further, the monolithic film can comprise a third region having a WVTR intermediate to that of the first and second regions. Still further, the film can comprise primarily a thermoplastic polymer and in a further aspect, can comprise at least a thermoplastic polymer and other components as desired.

In a further aspect of the invention, the methods of making monolithic films having regions of varied breathability are provided and can comprise providing a monolithic film having a hydrohead of at least 50 mbars and a WVTR of at least 800 g/m$^2$/24 hours and then selectively applying adhesives to a selected portion of said film thereby creating first and second regions therein. The WVTR is decreased within the second region of the monolithic film, i.e. the selected portion to which meaningful adhesives have been applied, relative to the WVTR of the first region. The second region can have minimum dimensions of at least 5 cm by 5 cm and desirably the second region comprises from about 5% to about 75% of the area of said film. In a preferred embodiment, adhesive is selectively applied to the monolithic film such that a pattern, continuous or discontinuous, of the second region is produced on the film.

Further aspects of the present invention will appear in the description hereinafter.

DEFINITIONS

The term "monolithic" is used herein to mean "non-porous", therefore a monolithic film is a non-porous film. Rather than holes produced by a physical processing of the monolithic film, the film has passages with cross-sectional sizes on a molecular scale formed by a polymerization process. The passages serve as conduits by which water (or other liquid) molecules can disseminate through the film. Vapor transmission occurs through a monolithic film as a result of a concentration gradient across the monolithic film. This process is referred to as activated diffusion. As water (or other liquid) evaporates on the body side of the film, the concentration of water vapor increases. The water vapor condenses and solubilizes on the surface of the body side of the film. As a liquid, the water molecules dissolve into the film. The water molecules then diffuse through the monolithic film and re-evaporate into the air on the side having a lower water vapor concentration.

As used herein the term "nonwoven" fabric or web means a web having a structure of individual fibers or threads which are interlaid, but not in an identifiable manner as in a knitted or woven fabric. Nonwoven fabrics or webs have been formed by many processes such as for example, meltblowing processes, spunbonding processes, hydroentangling, air-laid and bonded carded web processes.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, U.S. Pat. No. 5,382,400 to Pike et al., and U.S. Pat. No. 5,759,926 to Pike et al. Spunbond fibers are generally not tacky when they are deposited onto a collecting surface and are generally continuous.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers may be continuous or discontinuous, are generally smaller than 10 microns in average diameter, and are generally tacky when deposited onto a collecting surface.

As used herein "multilayer nonwoven laminate" means a laminate of two or more nonwoven layers such as, for example, wherein some of the layers are spunbond and some meltblown such as a spunbond/meltblown/spunbond (SMS) laminate. Examples of multilayer nonwoven laminates are disclosed in U.S. Pat. No. 4,041,203 to Brock et al., U.S. Pat. No. 5,178,931 to Perkins et al. and U.S. Pat. No. 5,188,885to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein, the term "machine direction" or "MD" means the length of a fabric or a product in the direction in which it is produced. The term "cross machine direction" or "CD" means the width of fabric or product, i.e. a direction generally perpendicular to the MD.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, "ultrasonic bonding" means a process performed, for example, by passing the fabric between a sonic horn and anvil roll as illustrated in U.S. Pat. No. 4,374,888 to Bornslaeger.

As used herein "point bonding" means bonding one or more layers of fabric at numerous small, discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen et al.

As used herein, the term "barrier" means a film, laminate or other fabric which is relatively impervious to the transmission of aqueous liquids and which has a hydrohead of at least about 50 mbar. Hydrohead as used herein refers to a measure of the aqueous liquid barrier properties of a fabric measured in millibars (mbar) as described herein below. However, it should be noted that in many applications of barrier fabrics, it may be desirable that they have a hydrohead value greater than about 80 mbar, 150 mbar or even 200 mbar.

As used herein, the term "breathability" refers to the water vapor transmission rate (WVTR) of an area of fabric which is measured in grams of water per square meter per 24 hours ($g/m^2/24$ hours). The WVTR of a fabric is the water vapor transmission rate which, in one aspect, gives an indication of how comfortable a fabric would be to wear. WVTR can be measured as indicated below and the results are reported in grams/square meter/24 hours.

As used herein the term "monocomponent" fiber refers to a fiber formed from one or more extruders using only one polymer. This is not meant to exclude fibers formed from one polymer to which additives have been added. As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers of a multicomponent fiber are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea" type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers and methods of making them are also taught in U.S. Pat. No. 5,382,400 to Pike et al. and may be used to produce crimp in the fibers by using the differential crystallization properties of the two (or more) polymers. The fibers may also have various shapes such as those described in U.S. Pat. No. 5,277,976 to Hogle et al., U.S. Pat. No. 5,466,410 to Hills and 5,069,970 and 5,057,368 to Largman et al.

As used herein the term "blend" means a mixture of two or more polymers while the term "alloy" means a sub-class of blends wherein the components are immiscible but have been compatibilized.

As used herein the term "biconstituent fibers" or "multiconstituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Bicomponent and biconstituent fibers are discussed in U.S. Pat. No. 5,294,482 to Gessner and in the textbook *Polymer Blends and Composites* by John A. Manson and Leslie H. Sperling, copyright 1976 by Plenum Press, a division of Plenum Publishing Corporation of New York, ISBN 0-306-30831-2, at pages 273 through 277.

As used herein, the term "scrim" means a lightweight fabric used as a backing material. Scrims are often used as the base fabric for coated or laminated products.

As used herein, the term "garment" means the same as the term "personal care product".

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets and the like.

As used herein, the term "personal care product" means personal hygiene oriented items such as diapers, training pants, absorbent underpants, adult incontinence products, feminine hygiene products, and the like.

As used herein the term "backsheet" refers to the aqueous liquid impervious protective layer on the garment side of a personal care product which prevents bodily exudates from escaping from the product.

As used herein, the term "protective cover" means a cover for vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths, picnic area covers, tents and the like.

DETAILED DESCRIPTION OF THE INVENTION

Figure 1A:
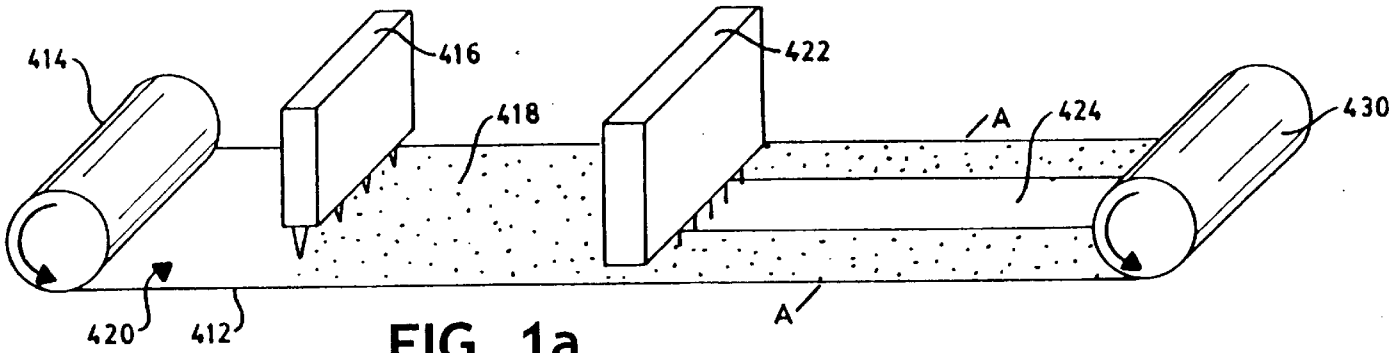
FIG. 1*a* is a schematic representation of an exemplary adhesive applicator assembly suitable for use in practicing the present invention and a zone treated monolithic film made therefrom.

Monolithic film is a non-porous film. Rather than holes produced by a physical processing of the monolithic film, the film has passages with cross-sectional sizes on a molecular scale formed by a polymerization process. The passages serve as conduits by which water (or other liquid) molecules can disseminate through the film. Vapor transmission occurs through a monolithic film as a result of a concentration gradient across the monolithic film. This process is referred to as activated diffusion. As water (or other liquid) evaporates on the body side of the film, the concentration of water vapor increases. The water vapor condenses and solubilizes on the surface of the body side of the film. As a liquid, the water molecules dissolve into the film. The water molecules then diffuse through the monolithic film and re-evaporate into the air on the side having a lower water vapor concentration.

As this is mainly a diffusion-rate limited phenomenon, the water vapor transmission rate (WVTR) is a function of the type of polymer used in the monolithic film and the thickness of the monolithic film. As such, the permeability is selective in monolithic films. Permeability can be increased or decreased by changing the chemical or structural characteristics of the polymers used in the construction of the film.

A monolithic film provides an absolute barrier to liquids, bacteria, and viruses as no pores are present in the film. However, distortion of the passages within a monolithic structure can cause elongation or deformation enabling viral pathogens to pass through the elongated opening of such passages. The liquid barrier properties of monolithic films are the result of the density of each type of monolithic film which prevents the passage of condensed liquids regardless of the viscosity or surface tension of the liquids. The liquid barrier properties are defined by burst strength, tensile properties, and abrasion resistance of each type of monolithic film as no liquid flow is possible unless the film ruptures.

The elasticity of a monolithic film are dependent upon the polymer used in the construction of the film. Examples of elastomers which can be used in a stretchable, breathable barrier application are thermoplastic (ether or ester) polyurethane, polyether-block-amides, and polyether-esters. These resins can be made into cast or blown films and then adhesively or thermally laminated to necked facings. They also can be extrusion coated onto necked spunbond to produce a stretchable laminate, similar to commercially available NBL.

Other advantages of monolithic films include water resistance, surfactant insensitive, selective permeability, high water entry pressure, variable water swelling, good tear strength, and excellent odor barrier.

The major advantage of monolithic films lies in their inherent breathability. Because of that, the monolithic films do not require the addition of fillers and stretching to generate micro-porosity. The benefit of this is threefold. First, intact monolithic films are absolute barriers to all liquids (including alcohol), bacteria, and viruses. The likelihood of defects within the monolithic film is reduced as holes are never intentionally introduced into the film.

Second, the in-elastic dead weight of filler is not added, the total mass of the film is available for elastic performance. The filler can also be a source of defects in microporous films.

And third, the elasticity of the film is not skewed by MD stretching, the excellent elastic properties of the polymer are fully maintained. Functional barrier and elastic films can be surprisingly thin, further enhancing breathability, thus, a low basis weight film can have excellent elastic properties and high breathability. Monolithic films are able to withstand high strain rates of being rapidly elongated to at least about 400% elongation. Micro-porous films shred under high strain rates.

A breathable monolithic film 412 can be treated, in accord with the present invention, to create a breathable film which can be used as a backsheet for personal care products, having regions of varied breathability using adhesives or other coating materials. The term "adhesive" or "adhesives" as used herein includes, but is not limited to, any material which will adhere to the breathable monolithic film when applied by some coating apparatus, thereby reducing the WVTR of the monolithic film where the adhesive has been applied.

Figure 1B:
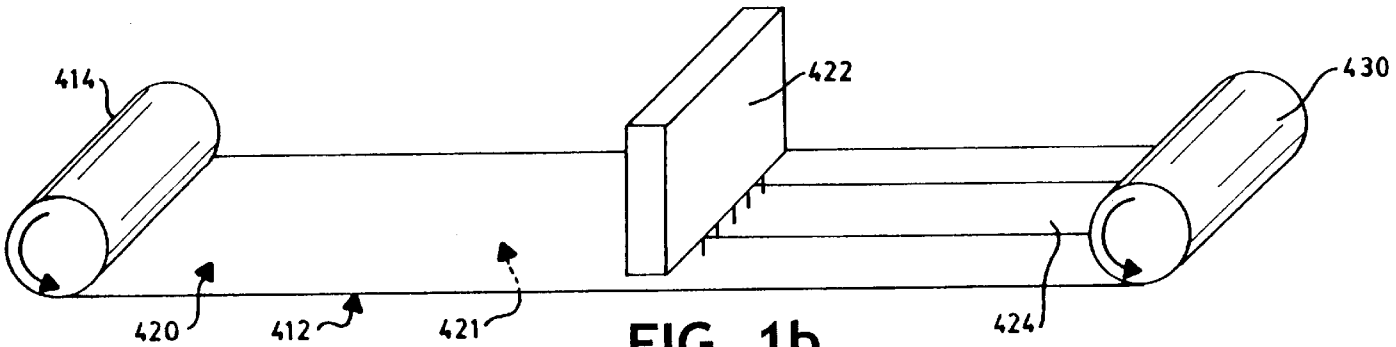
FIG. 1*b* is a schematic representation of an exemplary adhesive applicator assembly suitable for use in practicing the present invention and a zone treated monolithic film made therefrom.

In reference to FIGS. 1*a* and 1*b* monolithic film 412 is unwound from supply roll 414. A adhesive applicator 416 delivering an open patterned application, including but not limited to a Nordson Control Coat CC-200 available from the Nordson Corporation at Norcross, Ga., applies a construction adhesive layer 418 to the body-side surface 420 of the monolithic film 412. The construction adhesive layer 418 is applied in an open pattern and as such, has minimal effect on the breathability of the monolithic film 412. A second adhesive applicator 422, including but not limited to a Nordson EP45 contact type coating head available from the Nordson Corporation at Norcross, Ga., is used to apply an adhesive coat layer 424 on to areas where less breathability is desired.

Figure 2B:
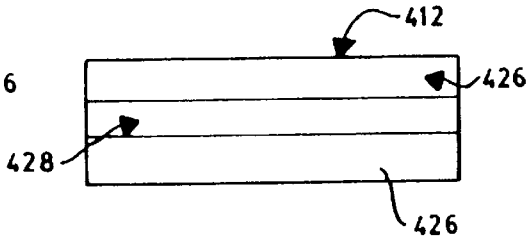
FIG. 2*b* is a plan view of a zone treated monolithic film suitable for use in practicing the present invention.
Figure 2A:
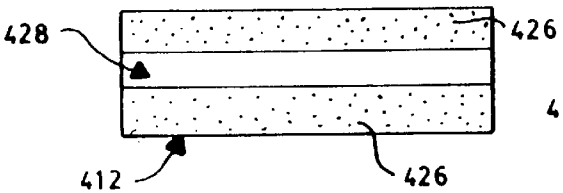
FIG. 2*a* is a plan view of a zone treated monolithic film suitable for use in practicing the present invention.

The amount of adhesive applied in the adhesive coat layer 424, as well as the type of adhesive and the type of adhesive application, depends on the desired reduction in breathability. The adhesive coat layer 424 applied to the monolithic film 412 at least partially covers or fills the openings of the passages within the monolithic film 412, thereby reducing the number of unoccluded openings of the passages within monolithic film 412 thereby reducing the breathability of the film in these selected areas. Thus, a breathable monolithic film 412 can be made having regions of controlled breathability. As shown in FIGS. 2*a* and 2*b* a monolithic film 412 is created having a first breathable regions 426 and second regions 428 having a breathability or WVTR lower than that of the first regions 426. The treated film 412 can then be wound on a winder roll 430 or further processed or converted as desired.

The construction adhesive layer 418 can be applied over the entire body-side surface 420 of the monolithic film 412 or the construction adhesive layer 418 can be applied in the areas only where the adhesive coat layer 424 will not be applied. The construction adhesive layer 418 is typically a construction adhesive, the adhesive used to attach the various components of product into which the monolithic film 412 is incorporated. The construction adhesive layer 418 preferably is from about 1 gsm to about 7 gsm, more preferably from about 2 gsm to about 5 gsm, and most preferably 3.2 gsm. An example of a construction adhesive is 34-5610 from National Starch and Chemical Company in Bridgewater, N.J.

In another embodiment of the present invention, a breathable monolithic film 412 can be treated, in accord with the present invention, to create a breathable film having regions of varied breathability using adhesives. In reference to FIGS. 1*a* and 1*b*, monolithic film 412 is unwound from supply roll 414. An adhesive applicator 422, including but not limited to a Nordson EP45 contact type coating head available from the Nordson Corporation at Norcross, Ga., is pulsed to apply an adhesive coat layer 424 on to areas where less breathability is desired. The amount of adhesive applied in the adhesive coat layer 424, as well as the type of adhesive and the type of adhesive application, determines the desired reduction in breathability. The adhesive coat layer 424 applied to the monolithic film 412 at least partially covers or otherwise occludes the openings of the passages within the monolithic film 412, thereby reducing the number of unoccluded openings of the passages within monolithic film 412 thereby reducing the breathability of the film in these selected areas. Thus, a breathable monolithic film 412 can be made having regions of controlled breathability. As shown in FIGS. 2*a* and 2*b*, a monolithic film 412 is created having a first breathable regions 426 and second regions 428 having a breathability or WVTR lower than that of the first regions 426. The treated film 412 can then be wound on a winder roll 430 or further processed or converted as desired.

While it may be typical to apply the adhesive coat layer 424 to the body-side surface 420 of the monolithic film 412, the adhesive coat layer 424 may be applied to the garment-side surface 421 of the monolithic film 412 as it is incorporated into absorbent garments. The garment side surface 421 of the monolithic film refers to the surface of the monolithic film 412 that will face away from the wearer, toward the wearer's clothes when the monolithic film 412 is incorporated into the breathable absorbent garment.

Suitable monolithic films for practicing this embodiment of the present invention include breathable monolithic films having a WVTR of at least 800 g/m$^2$/24 hours, and more desirably having a WVTR in excess of 1500 g/m$^2$/24 hours, 2500 g/m$^2$/24 hours or 3500 g/m$^2$/24 hours. Desirably, the breathable monolithic film substrate has a WVTR between about 2000 g/m$^2$/24 hours and about 7000 g/m$^2$/24 hours. The breathable monolithic films preferably have a film thickness less than about 100$\mu$ (microns) and desirably have a thickness less than about 50$\mu$ and more desirably have a thickness between about 10 and about 35$\mu$. Thin breathable monolithic film can be formed by any one of various methods known in the art. Examples of breathable films suitable for use with the present invention include, but are not limited to, those described in the following references: U.S. Pat. No. 5,679,373 issued Oct. 21, 1997 to Wick et al.; U.S. Pat. No. 5,682,618 issued Nov. 4, 1997 to Johnson et al.; U.S. Pat. No. 5,656,167 issued Aug. 12, 1997 to Martz; U.S. Pat. No. 5,762,643 issued Jun. 9, 1998 to Ray et al.; U.S. Pat. No. 5,653,699 issued Aug. 5, 1997 to Reed et al.; U.S. Pat. No. 5,589,249 issued Dec. 31, 1996 to Bodford et al.; U.S. Pat. No. 5,521,273issued May 28, 1996 to Yilgor et al.; U.S. Pat. No. 5,417,984 issued May 23, 1995 to Banker et al.; U.S. Pat. No. 5,328,757 issued July 12, 1994 to Kenney et al.; U.S. Pat. No. 5,190,533 issued Mar. 2, 1993 to Blackburn; and, U.S. Pat. No. 4,076,895 issued Feb. 28, 1978 to Theno; the entire contents of the aforesaid references are incorporated herein by reference.

Some of the commercially available monolithic films include: polyesters, including copolymers of various cyclic polyesters sold under the tradename Hytrel, including the 4056 grade from the E. I. DuPont de Nemours and Company of Wilmington, Del., sold under the trademark LOMOD from General Electric, and sold under the trademark PCCE from the Eastman Chemical; polyether block amide elastomeric resins sold under the trademark PEBAX from the Elf Atochem S.A. in France; thermoplastic polyurethanes, including polyether polyurethanes: sold under the trademark PELLETHANE, including the 2363-80 AE grade from the Dow Chemical Company of Midland, Mich., sold under the trademark Q-THANE from the K. J. Quin, sold under the trademark ESTANE, including the 58661 grade from the B. F. Goodrich, and sold under the trademark TXIN from Mobay Chemical Company; and, ethylene methacrylic and acrylic acid copolymers sold under the commercial designation Nucrel 699.

A preferred breathable monolithic film can comprise a thermoplastic polymer. These (and other) components can be mixed together, heated and then extruded into a monolayer or multilayer film. The film may be made by any one of a variety of film forming processes known in the art such as, for example, by using either cast or blown film equipment. Suitable films can also include multilayer films having at least one monolithic layer.

Monolithic films include poly-ethylenes (such as low density polyethylene), ethylene methyl acrylate copolymers, and ethylene vinyl acetate copolymers. One type of monolithic film comprises a copolyester thermoplastic elastomer such as a copolyetherester elastomer having a randomized hard-soft segment structure which is permeable to polar molecules such as water but is resistant to penetration by non-polar hydrocarbons such as refrigerant gases.

Another type of monolithic film comprises thermoplastic polyurethane elastomers which are basically diisocynates and short chain diols (forming the basis of the hard segments) and long chain diols (forming the basis of the soft segments). Because the hard and soft segments are incompatible, the thermoplastic urethane elastomers exhibit two-phase structures which in turn cause the formation of domain microstructures.

Another type of monolithic film is a polyamide thermoplastic elastomer comprising hard and soft segments joined by amide linkages. These thermoplastic polyamide elastomers exhibit properties that are dependent upon the chemical composition of the hard (polyamide) and the soft (polyether, polyester, or polyetherester) segments as well as the length of the segments.

Still another type of monolithic film is a polymer/polymer composite combining polydimethyl siloxane and polytetrafluoroethylene in an interpenetrating polymer network. The film is a physical blend of the two polymers rather than a copolymer or a new compound.

The monolithic films can comprise known film forming polymers which are, by mechanical and/or thermal treatment, permanently deformable. Mechanically deformable polymer films are believed to be suitable for use with the present invention (e.g. soft rubbers). Desirably the monolithic film is made from a thermoplastic polymer. Preferred thermoplastic polymers used in the monolithic films of the present invention include, but are not limited to, polyolefins including homopolymers, copolymers, terpolymers and blends thereof. Additional film forming polymers suitable for use with the present invention, alone or in combination with other polymers, include ethylene vinyl acetate, ethylene ethyl acrylate, ethylene acrylic acid, ethylene methyl acrylate, ethylene normal butyl acrylate, polyester, polyethylene terephthalate, polyamides (e.g. nylon), ethylene vinyl alcohol, polystyrene, polyurethane, polybutylene, and polybutylene terephthalate. However, polyolefin polymers are preferred such as, for example, polymers of ethylene and propylene as well as copolymers, terpolymers and blends thereof; examples include, but are not limited to, linear low density polyethylene (LLDPE) and ethylene-propylene copolymer blends. The monolithic films can comprise elastic or inelastic polymers.

Once the breathable monolithic film 412 has been formed, the monolithic film 412 can be treated to impart zoned or controlled regional breathability to the monolithic film 412. The monolithic film 412 can be made in-line or made previously and unwound from a supply roll. Selected regions of the monolithic film 412 are treated with sufficient adhesive to at least partially cover or fill the openings of the passages of the monolithic film 412, thereby reducing the number of unoccluded openings of the passages therein and thereby reduce and/or substantially eliminate the breathability previously imparted to the monolithic film 412 in the treated region. The breathability is directly dependent upon the thickness of the adhesive (the amount of adhesive continuity, and percentage of coverage), the type of adhesive used, and the type of adhesive application used in applying the adhesive coat layer 424 to the monolithic film 412. The thicker or more uniform the adhesive coat layer 424 applied to the monolithic film 412, the more openings of the passages within the monolithic film 412 will be covered or otherwise occluded, thereby reducing the breathability of the monolithic film 412. Thus, the breathability of the monolithic film 412 can be varied by varying a combination of any or all of the following factors: the thickness of the adhesive coat layer 424 (the amount of adhesive continuity and percentage of coverage), the type of adhesive used in the adhesive coat layer 424, and the type of adhesive application used to apply the adhesive coat layer 424 to the monolithic film 412.

The treated regions of the monolithic film 412 extend at least 3 cm in the CD and MD and more desirably at least 5 cm×5 cm in the CD and MD. Further, the treated regions of the surface can extend at least 10 cm in either the CD or MD direction. In a further aspect of the invention, the treated regions desirably comprise from about 5% to about 90% of the area of the monolithic film 412. In a preferred embodiment of the present invention the treated regions comprise a contiguous area comprising from about 5% to about 75% of the area of the overall monolithic film 412 and more desirably comprise from about 15% to about 60% of the area of the monolithic film 412. In a further embodiment, the regions can comprise a plurality of regions of intermediate and low breathability. The regions of low and intermediate breathability desirably form a single contiguous area and which can, in one aspect, be disposed about the central portion of the monolithic film 412. However, the treated regions can comprise several non-contiguous regions and needs not be centered on the breathable film 412.

Figure 3A:
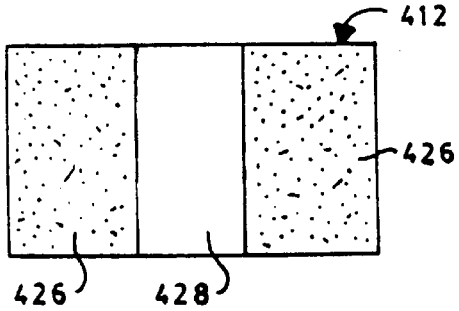
FIG. 3*a* is a plan view of a zone treated monolithic film suitable for use in practicing the present invention.
Figure 3B:
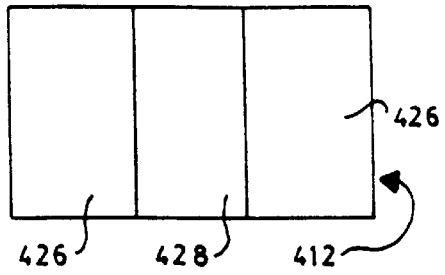
FIG. 3*b* is a plan view of a zone treated monolithic film suitable for use in practicing the present invention.
Figure 4A:
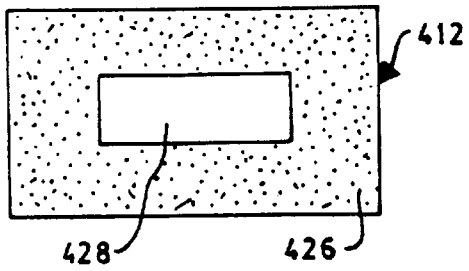
FIG. 4*a* is a plan view of a zone treated monolithic film suitable for use in practicing the present invention.
Figure 4B:
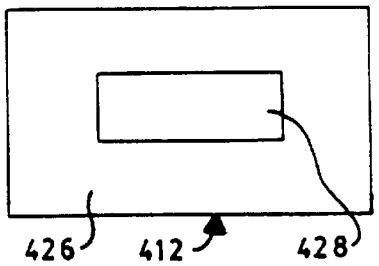
FIG. 4*b* is a plan view of a zone treated monolithic film suitable for use in practicing the present invention.

In one embodiment of the present invention, the adhesive coat layer 424 can be applied in a continuous pattern as seen in second regions 428 in FIG. 2*a*. The adhesive coat layer 424 can also be applied such that a continuous second region 428 is disposed in the center of the monolithic film 412, creating a zoned breathability monolithic film 412, such as shown in FIGS. 3*a* and 3*b* having highly breathable regions 426 adjacent the opposed edges of the monolithic film 412 and a central second region 428 of reduced breathability therebetween. The reduced breathability region 428 can extend continuously in the machine direction of the monolithic film 412 In a further aspect of the invention, the thickness (amount or percentage of coverage) of the adhesive coat layer 424 can be varied in order to further modify the breathability of the corresponding region of the monolithic film 412. Varying the thickness of the adhesive coat layer 424 results in varied levels of breathability extending in the machine direction.

Varying the thickness (including amount or percentage of coverage by the adhesive coat layer 424) is one method of controlling the breathability of the monolithic film 412. Other methods include changing the method of application of the adhesive coat layer 424. For example, a meltblown application of 3.2 gsm of adhesive onto the monolithic film 412 has very little effect on the WVTR of the monolithic film 412. However, the slot coating application of 3.2 gsm of adhesive onto the monolithic film 412 has a marked effect on the WVTR of the monolithic film 412.

Figure 5A:
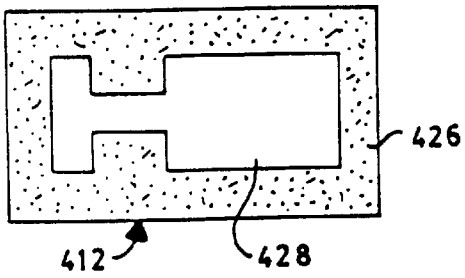
FIG. 5*a* is a plan view of a zone treated monolithic film suitable for use in practicing the present invention.
Figure 5B:
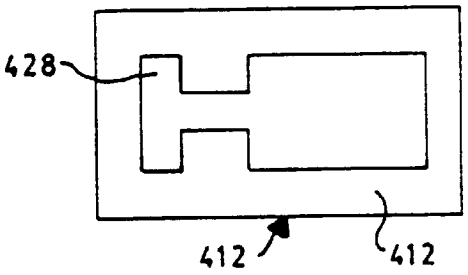
FIG. 5*b* is a plan view of a zone treated monolithic film suitable for use in practicing the present invention.
Figure 6:
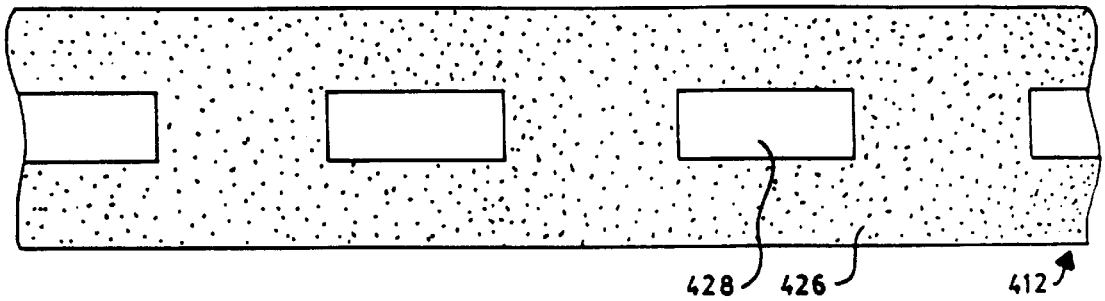
FIG. 6 a schematic representation of an adhesive application pattern suitable for use in practicing the present invention.

In a further aspect of the invention, the adhesive coat layer 424 can be applied so as to create shaped regional breathability to the monolithic film 412. In reference to FIGS. 5*a* and 5*b* the adhesive coat layer 424 can be applied in second regions 428 having different WVTRs. Thus, the monolithic film 412 is thereby created having first region 426 and second region 428 wherein first region 426 has a higher WVTR than second region 428.

In a further aspect, the application of the adhesive coat layer 424 can be discontinuous in the sense that the adhesive is applied in a broken pattern as shown in FIGS. 4*a*, 4*b*, 5*a*, 5*b*, and 6. The treatment of a monolithic film 412 as such create first region 426 and second region 428 whereby first region 426 has greater breathability than second region 428. Further, second region 428 will be separated by portions of first region 428 in the machine direction.

Figure 7:
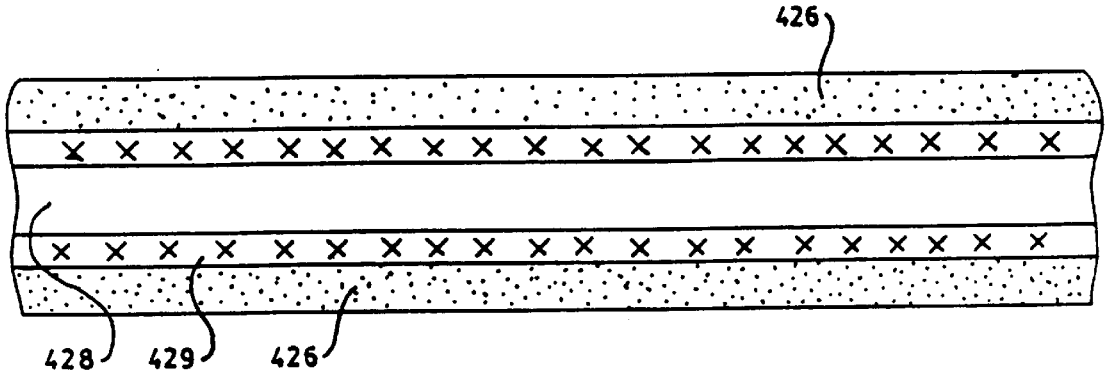
FIG. 7 is a schematic representation of an adhesive application pattern suitable for use in practicing the present invention.

As a further example, the adhesive coat layer 424 can be applied in a manner to create a breathability gradient across the CD of the monolithic film 412. In reference to FIG. 7, one such configuration can result in a zoned monolithic film 412 having a first region 426 of high breathability, second region 428 of low breathability and third region 429 of intermediate breathability. The adhesive coat layer 424 applied in the second region 428 is thicker (an increased amount or a higher percentage of coverage of the adhesive coat layer 424) than the adhesive coat layer 424 applied the third region 429, resulting in a breathability gradient. By varying the thickness of the adhesive coat layer 424 in the CD of the monolithic film 412, a breathability gradient having regions of varied breathability across the CD of the monolithic film 412 is created as opposed to substantially distinct regions of breathability.

As a further example, the adhesive coat layer 424 can be applied in a manner to create a breathability gradient across the CD of the monolithic film 412. In reference to FIG. 7, one such configuration can result in a zoned monolithic film 412 having a first region 426 of high breathability, second region 428 of low breathability and third region 429 of intermediate breathability. The adhesive coat layer 424 applied in the second region 428 is of a different type of adhesive for use in the adhesive coat layer 424 applied in the third region 429, resulting in a breathability gradient. By varying the type of the adhesive coat layer 424 in the CD of the monolithic film 412, a breathability gradient having regions of varied breathability across the CD of the monolithic film 412 is created as opposed to substantially distinct regions of breathability.

As a further example, the adhesive coat layer 424 can be applied in a manner to create a breathability gradient across the CD of the monolithic film 412. In reference to FIG. 7, one such configuration can result in a zoned monolithic film 412 having a first region 426 of high breathability, second region 428 of low breathability and third region 429 of intermediate breathability. The adhesive coat layer 424 applied in the second region 428 under a different method of adhesive application of the adhesive coat layer 424 than used to apply the adhesive coat layer 424 to the third region 429, resulting in a breathability gradient. By varying the type of adhesive application of the adhesive coat layer 424 in the CD of the monolithic film 412, a breathability gradient having regions of varied breathability across the CD of the monolithic film 412 is created as opposed to substantially distinct regions of breathability.

The zoned treatment of the monolithic film 412 acts to at least partially cover or otherwise occlude the openings of the passages within the monolithic film 412, thereby reducing the number of unoccluded openings of the passages within in the treated regions thereby reducing the WVTR or breathability in those same regions. In reference to FIGS. 2*a* and 2*b,* the zone treated monolithic film 412 can have a first substantially untreated region 426 which has a higher level of breathability than the second adhesively treated region 428 of the monolithic film 412. It is understood that the phrase "substantially untreated region" refers herein to regions that may have undergone a treatment, however the treatment had little or no effect on the WVTR of the monolithic film 412. The second region 428 will substantially correspond to those areas of the monolithic film 412 to which an adhesive coat layer 424 has been applied.

In a further aspect of the invention, the zoned breathability monolithic film 412 can be joined with one or more additional layers. Alternatively, additional layers can be attached to the monolithic film prior to zone treating the monolithic film 412. Desirably the monolithic film 412 is attached to a pliable support layer capable of being laminated to the monolithic film 412 such as, for example, a pliable fibrous, film and/or foam material. Exemplary fibrous layers include, but are not limited to, nonwoven webs, multilayer nonwoven laminates, scrims, woven fabrics, slit films and/or other like materials. Desirably the support fabric comprises one or more layers of spunbonded and/or meltblown fiber webs including, but not limited to, monocomponent spunbond fiber webs, multicomponent spunbond fiber webs, split fiber webs, multilayer nonwoven laminates, bonded carded webs and the like. Typically, these fibrous layers are highly breathable and do not impair the breathability of the monolithic film 412 when attached to the monolithic film 412. Generally, the composition of the fibrous layer may be selected to achieve the desired properties, i.e. hand, aesthetics, tensile strength, cost, abrasion resistance, hook engagement, etc. It is understood that the bonding means used to attach the fabric layer to the monolithic film 412 should not impair the breathability of the monolithic film 412. This concern is not as great in areas where reduced WVTR is desired.

Further, the fibrous layer can also be treated such as, for example, by embossing, hydroentangling, mechanically softening, printing or treated in another manner in order to achieve additional desired characteristics. In one embodiment the outer layer may comprise about a 10 g/m$^2$ to about 68 g/m$^2$ web of spunbonded polyolefin fibers and even more desirably a 10 g/m$^2$ to about 34 g/m$^2$ web of such fibers. The fibrous layer can be attached or laminated to the monolithic film 412 by adhesive bonding, thermal bonding, ultrasonic bonding or other means known in the art. In one aspect of the invention the monolithic film 412 and fibrous layer are bonding with an adhesive sprayed via a standard meltblown die to either the nonwoven fabric and/or monolithic film 412. In a further aspect of the invention, the fibrous layer and monolithic film 412 can be laminated via thermal point bonding.

The monolithic films 412 of the present invention having controlled regional breathability can be used with a wide variety of products or as components of products such as, for example, in personal care articles, infection control products, protective covers, garments and the like. As a particular example, a monolithic film 412 similar to that shown in to FIGS. 2*a,* 2*b,* 3*a,* 3*b,* 4*a,* 4*b,* 5*a,* 5*b,* 6, and 7 can be readily converted and incorporated within a breathable barrier of a diaper or incontinence garment whereby the regions of reduced breathability of the monolithic film 412 extend along the central portion or crotch of the diaper. The regions more or less coextensive with the absorbent pad 58 are typically of lower breathability, while regions typically of higher breathability extend along the outer portions or "ears" of the garment where the absorbent pad 58 is typically not present to maximize dryness or skin health. In a further example, the zoned breathability monolithic films 412 may be used in surgical gowns. It is believed that the regions of reduced breathability, particularly areas where breathability has been significantly or almost completely reduced, may provide improved barrier properties. For example, areas of reduced breathability are believed to provide improved barrier properties to blood borne pathogens. Thus, surgical gowns can be fabricated employing the treated or low breathability regions within high risk areas, such as the forearms of the gown, and higher WVTR regions within lower risk areas. The monolithic film 412 can also be advantageously utilized in numerous other applications employing breathable barrier fabrics.

Figure 8:
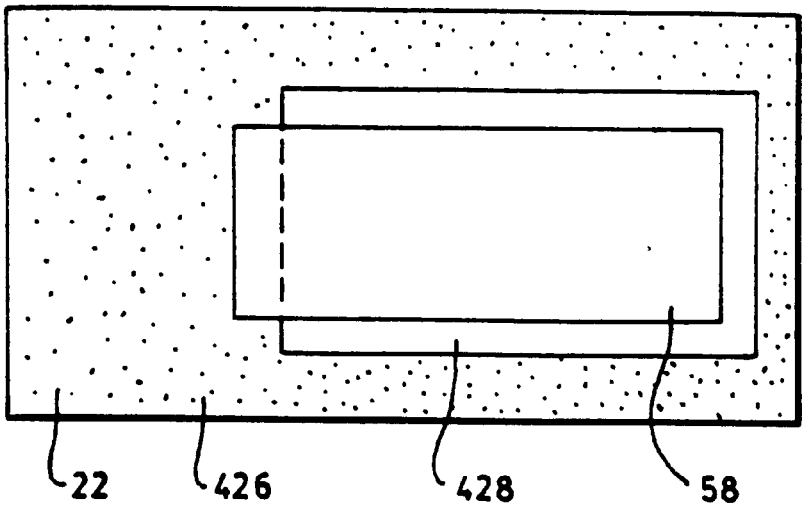
FIG. 8 is a plan view of a zone treated monolithic film suitable for use in practicing the present invention and placement of an absorbent pad thereon.
Figure 9:
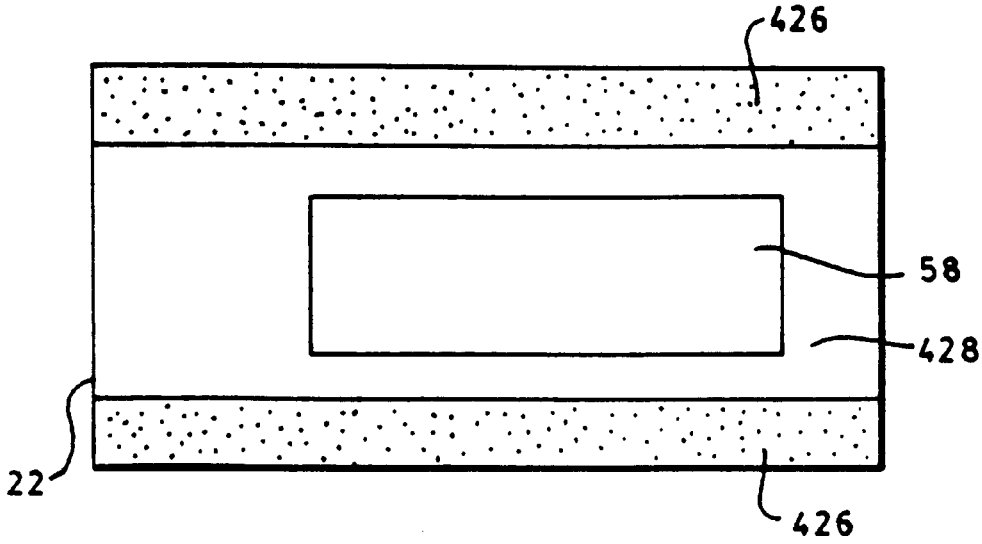
FIG. 9 is a plan view of a zone treated monolithic film suitable for use in practicing the present invention and placement of an absorbent pad thereon.
Figure 10:
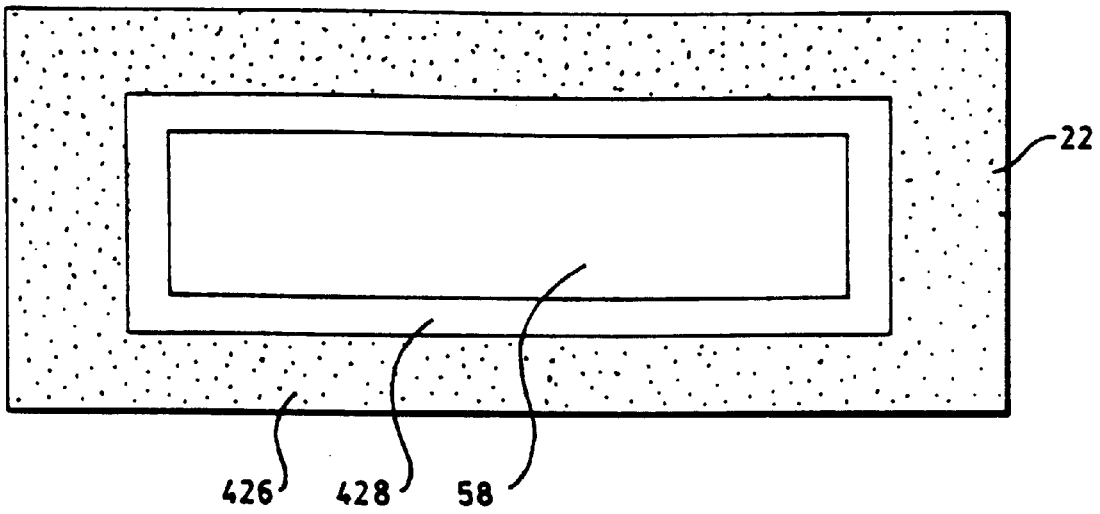
FIG. 10 is a plan view of a zone treated monolithic film suitable for use in practicing the present invention and placement of an absorbent pad thereon.
Figure 11:
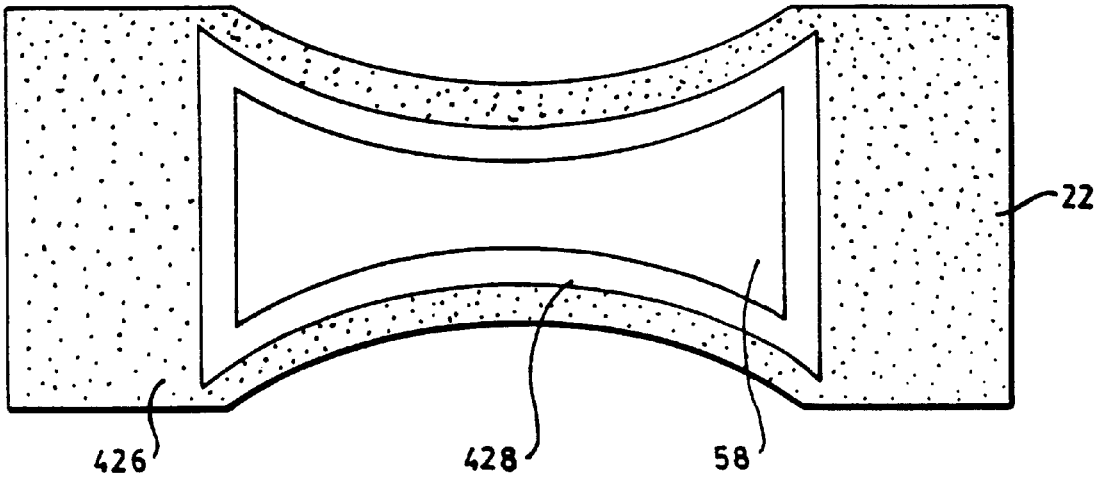
FIG. 11 is a plan view of a zone treated monolithic film suitable for use in practicing the present invention and placement of an absorbent pad thereon.

FIG. 8 shows that the absorbent pad 58 need not cover the entire second region 428 and that the absorbent pad 58 may overlap onto a portion of the first region 426. Typically the portion of the absorbent pad 58 which has the highest aqueous liquid loading is positioned over the second region 428. FIG. 9 shows the zone treated monolithic film 412 of FIGS. 1*a* and 2*a* including an absorbent pad 58 having smaller dimensions than the second region 428. FIGS. 2*a* and 2*b* show such monolithic film 412. FIG. 10 shows the absorbent pad 58 as not covering the entire second region 428. FIG. 11 shows an alternate embodiment as shown in FIG. 10 including a shaped monolithic backing member 22 and absorbent pad 58 which have leg cutouts typically included for improved fit and comfort. (See FIGS. 5*a* and 5*b*). However, the size and/or shape of the absorbent pad 58 may coincide with the size and/or shape of the second region 428.

In some embodiments, the present invention is a method of making a monolithic film 412 having regions of varied breathability. The method comprises: providing a monolithic film 412 wherein the monolithic film 412 has a hydrohead of at least 50 mbars and a WVTR of at least 800 g/m$^2$/24 hours; selectively applying adhesive to a portion of the monolithic film 412 thereby creating first and second regions 426 and 428 within the monolithic film 412, the second region having dimensions of at least 3 cm by 3 cm wherein the WVTR is decreased within the second region 428 of the monolithic film 412 relative to the WVTR of the first region 426.

Variations of the present invention in other embodiments may include any of the following: The step of providing the monolithic film 412 may comprise the steps of providing a monolithic film 412 wherein the application of adhesive may decrease the WVTR of the second region 428 by at least 25% and further wherein the second region 428 has a minimum dimensions of 5 cm by 5 cm. The second region 428 may comprise from about 5% to about 75% of the area of the monolithic film 412. The thermoplastic polymer may comprise a polyolefin polymer and wherein the basis weight of each of said first and second regions 426 and 428 may be below about 35 g/m$^2$. The adhesive may be selectively applied to the monolithic film 412 in a coat layer. The second region 428 may comprise between about 5% and 75% of the area of the monolithic film 412 and further wherein the first and second regions 426 and 428 of the monolithic film 412 each have a basis weight less than about 35 g/m$^2$. The step of providing the monolithic film 412 may further comprise the step of providing a monolithic film 412 having a basis weight less than about 35 g/m$^2$ and a WVTR in excess of 1500 g/m$^2$/24 hours and further wherein the WVTR of the second region 428 may be decreased by at least 50%. For example, the adhesive applied to the monolithic film 412 may comprise a first thickness and a second thickness wherein the first region 426, the second region 428, and the third region 429 may be created within the monolithic film 412 with the third region having a WVTR intermediate to the WVTR of the first and second regions 426 and 428. The second region 428 may comprise from about 5% to about 75% of the monolithic film 412. The second region 428 and the third region 429 may be continuous. The monolithic film 412 may have a WVTR gradient. The method may further comprise the step of laminating a nonwoven web to the monolithic film 412 prior to applying the adhesive.

Test Methods

Hydrohead: A measure of the liquid barrier properties of a fabric is the hydrohead test. The hydrohead test determines the height of water or amount of water pressure (in millibars) that the fabric will support before aqueous liquid passes therethrough. A fabric with a higher hydrohead reading indicates it has a greater barrier to aqueous liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as noted below. The hydrohead was determined using a hydrostatic head tester available from Marl Enterprises, Inc. of Concord, N.C. The specimen is subjected to a standardized water pressure, increased at a constant rate until the first sign of leakage appears on the surface of the fabric in three separate areas. (Leakage at the edge, adjacent clamps is ignored.) Unsupported fabrics, such as a thin film, are supported to prevent premature rupture of the specimen.

WVTR: The water vapor transmission rate (WVTR) for the sample materials was calculated in accordance with ASTM Standard E96-80. Circular samples measuring three inches in diameter were cut from each of the test materials and a control which was a piece of CELGARD™ 2500 film from Hoechst Celanese Corporation of Sommerville, N.J. CELGARD™ 2500film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C.) for 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

$$\text{Test WVTR}=(\text{grams weight loss over 24 hours})\times 315.5\ \text{g/m}^2/24\ \text{hours} \quad \text{(I)}$$

The relative humidity within the oven was not specifically controlled.

Under the predetermined set conditions of 100° F. (32° C.) and ambient relative humidity, the WVTR for the CELGARD™ 2500 control has been defined to be 5000 grams per square meter for 24 hours. Accordingly, the control sample was run with each test and the preliminary test values were corrected to set conditions using Equation (II) below:

$$\text{WVTR}=(\text{Test WVTR/control WVTR})\times(5000\ \text{g/m}^2/24\ \text{hours}) \quad \text{(II)}$$

Strip Tensile: The strip tensile test measures the peak and breaking loads and peak and break percent elongations of a fabric. This test measures the load (strength) in grams and elongation in percent. In the strip tensile test, two clamps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Results are reported as an average of three specimens and may be performed with the specimen in the cross direction (CD) or the machine direction (MD).

EXAMPLE I

A monolithic film may be laminated to a non-woven fabric to form an outer cover. Adhesive is then added to the film side of the outer cover laminate (which faces the wearer's body when incorporated in an absorbent garment) to create two breathable zones. Adhesive is applied through a meltblown application at a level of 3.2 gsm was applied continuously, the full length of the article. A second adhesive head is used to apply adhesive, generally the length and width of the absorbent core, through a slot die at the same and higher add-on rates. The first adhesive system is designed to have minimal effect on the film WVTR while the second system is designed to substantially reduce it. The potential adhesive has the designation 34-5610 from National Starch and Chemical Company in Bridgewater, N.J.

EXAMPLE II

Figure 12:
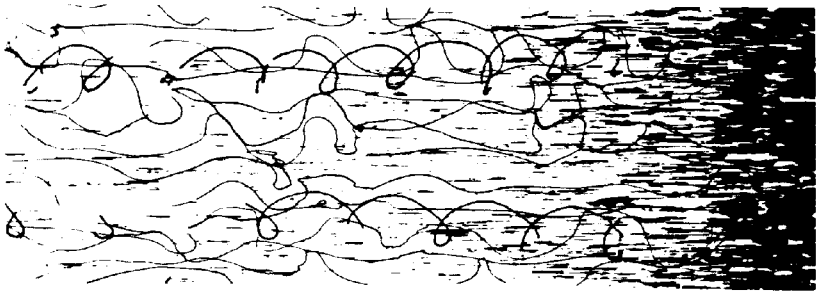
FIG. 12 is a plan view representation of a treated monolithic film leaving an open adhesive pattern with minimal effect on the WVTR of the film.
Figure 13:
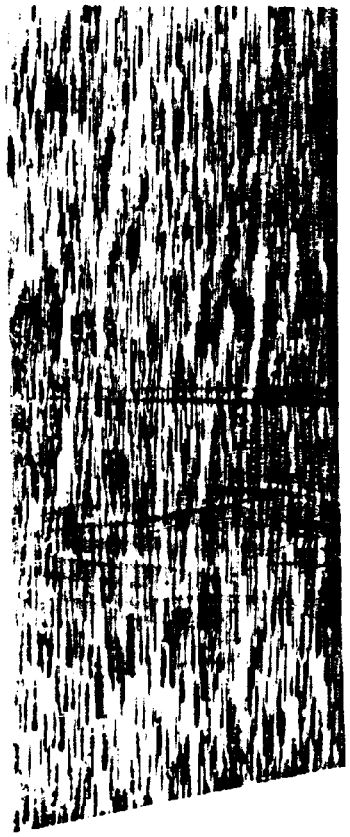
FIG. 13 is a plan view representation of a treated microporous film having an adhesive coat layer with significant reduction of the WVTR of the film.
Figure 14:
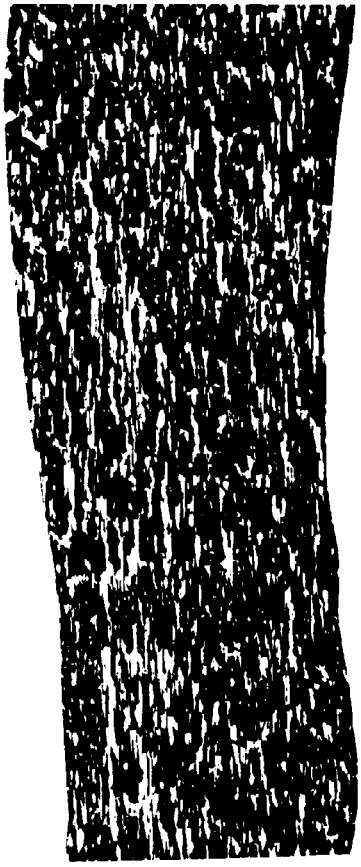
FIG. 14 is a plan view representation of a treated microporous film having an adhesive coat layer with significant reduction of the WVTR of the film.

FIG. 12 shows a microporous film with a meltblown adhesive coverage of about 8%. This would result in the WVTR dropping from about 4200 to about 3900. FIG. 13 shows a microporous film with a coat layer coverage of about 24% which would be expected to result in about a larger WVTR drop than the 8% coverage, but a smaller WVR drop than the 70% coat layer coverage. FIG. 14 shows a 70% coat layer coverage which resulted in a larger WVTR drop. These show results that would be similar for monolithic films.

EXAMPLE III

It has been found that slot coating applied to a non-woven web has less effect on the laminate WVTR than applying to a film. A slot coater, therefore could be used to maintain high WVTR in the desired product regions if slot coating is applied to a non-woven like fabric rather than onto the microporous film.

An equal amount of construction adhesive (34-5610 from National Starch and Chemical Company in Bridgewater, N.J.) is applied via slot coating onto both a non-woven fabric (0.75 osy, sheath/core, 50/50 polypropylene polyethylene spunbond) and a microporous film having a high WVTR (in excess of 3,500). It would be expected that a smaller reduction in WVTR would occur when the non-woven is slot coated as compared to when the film is slot-coated. Similar results would be expected with monolithic films.

| Film WVTR | Laminate WVTR When Slot Coated onto Non-woven |
|---|---|
| 4,270 | 4,080 |
| **Laminate WVTR** | **WVTR When Slot Coated onto Film** |
| 4,080 | 3,500 |

EXAMPLE IV

It has been found that neither a meltblown (also referred to as MB) nor swirl adhesive application lower the WVTR of a microporous film significantly at adhesive levels up to 3.2 gsm of 34-5610 adhesive. It would be expected that similar results would be expected when a monolithic films is used in place of the microporous film.

| Description | WVTR |
|---|---|
| Film | 4,266 |
| 3.2 gsm MB on nonwoven | 4,178 |
| 1.6 gsm MB on film | 4,317 |
| 3.2 gsm Swirl on film | 4,063 |
| 1.0 gsm Swirl on film | 4,486 |

EXAMPLE V

This example demonstrates that high WVTR values can result in condensation of water vapor on the outer surface of an absorbent garment. This is perceived as leakage by many consumers. The test was completed on microporous films. However, similar results would be expected on using monolithic films.

Panelists evaluated the materials in a blind comparison using the following test method. Before evaluation, all samples were loaded with 240 ml of body temperature saline, and placed on a heating pad also warmed to body temperature for two hours. Each diaper was placed inside a black box for a blind evaluation. All participants evaluated each material by feeling it four times as presented to them in a randomly ordered sequence. Each material was evaluated independently. The study included three codes. Panelists evaluated a total of twelve diapers (3 codes×4 repeats= 12 diapers) with a fifteen minute break after evaluating six diapers to help reduce hand fatigue.

| Product | WVTR of Outer Cover | Front Moisture Rating | Back Moisture Rating |
|---|---|---|---|
| A | 1,650 | 15.9 | 22.1 |
| B | 2,715 | 18.8 | 24.1 |
| C | 4,125 | 20.9 | 26.3 |
| D | 0 | 12 | 18 |

Products A, B, C, and D (a standard reference) HUGGIES® were commercially available diapers in which the outer covers were replaced with over covers having the stated WVTR.

EXAMPLE VI

This example demonstrates that high WVTR levels in nonabsorbent areas of a disposable garment increase wearer comfort. The disposable garments tested were commercially available DEPEND® Undergarments which were modified with outer covers of differing breathability. The test was conducted on a KES-F7 Thermo-Lobo IIB Type equipment available from Kato-Tech Co, LTD., in Kyoto, Japan. The test method is described in the operating manual for the equipment.

The ability of moisture and heat to permeate through fabric is a significant factor in determining how comfortable a garment will be. Heat can be transferred through a fabric in two ways: dry heat transfer and/or moisture-assisted heat transfer. From the dry and wet heat transfer rate measurements, the permeability index (Im), can be calculated. The KES Thermo-labo test measures the dry and wet heat transfer rates of a material using a guarded or sweating hot plate. It also measures how warm or cool a material feels to the touch and the thermal conductivity of materials.

The characteristic values shown from the KES Thermo-labo test are described below.

Wet Heat Transfer represents the amount of heat that is transferred from the skin through the fabric to the outside environment with the assistance of moisture. The larger the wet heat transfer value, the more heat will be lost or transferred through the fabric with the assistance of moisture. This test is appropriate for the measurement of heat transfer in most situations where the wearer would perspire.

Im or Permeability Index is the ratio of the thermal and evaporative resistance of the fabric to the ratio of thermal and evaporative resistance of air. As the value approaches 1, the less resistant or more air-like the fabric is. For example, a lightweight, loosely woven fabric would have a larger Im value than Tyvek. (Differences as small as 0.01 can be perceived.)

| | Non-breathable non-microporous film | 1,200 WVTR microporous film | 2,500 WVTR microporous film | 3.5 osy Woven Cotton |
|---|---|---|---|---|
| Wet Heat Transfer (Watts/m2) | 7.72 | 8.87 | 11.94 | 18.4 |
| Im or Permeability Index | 0.18 | 0.23 | 0.39 | 0.59 |

EXAMPLE VII

This example demonstrates that high WVTR levels in certain areas of a disposable garment increase wearer skin wellness by reducing skin occlusion and excessive hydration of the skin.

Undergarments that were modifications of commercially available DEPEND® Undergarments, were tested with 20 panelists. The modifications included shortening the absorbent core from 21 inches to 19 inches (centered on the outer cover) and incorporating new outer covers with the stated WVTRs. The outer covers consisted of a film (either non-porous or monolithic) and a nonwoven laminated to the film.

Skin conductance measurements were taken on the panelist's lower back in a region where the garment's body-side liner and outer cover covered the skin (not in a region where the absorbent core was present).

The skin conductance readings were taken with a Skicon 200 instrument such as that available from ACA DERM of Mento Park, Calif. Panelists were given a short sleeve disposable lab coat, made of polypropylene spunbond, cotton sweatpants, and a pair of cotton underwear to wear during the test period. Panelists were then allowed to acclimate to the environment which was controlled to approximately 72° F./43% R.H. for 10–15 minutes. After acclimation, the panelists lay on their stomachs, their clothing over their lower back was peeled down, and a Baseline skin conductance reading was taken using the Skicon.

Subsequently, the panelists were given an undergarment to don, under their underwear and sweatpants. The total wear time of the undergarment was 1.5 hours. During the first ten minutes of wear time, the panelists participated in a moderate exercise of their choice (such as walking, treadmill, stationary bike, aerobic activity). The next twenty minutes, the panelists rested. They exercised the next ten minutes (30–40 minutes into wear time), rested the next 20 minutes (40–60 minutes into weartime), exercised the next ten minutes (60–70 minutes into wear time), and finally rested the last twenty minutes of the 1.5 hour undergarment weartime.

After the 1.5 hour wear time, a post-wear skin conductance reading was taken in the same manner and region as the baseline reading.

The change in skin conductance, from the baseline to post wear regions, represents the change in skin hydration during that period. The data shows that the non-breathable product resulted in a much greater increase in skin hydration than the breathable products. Such increases over time lead to wearer discomfort and reduced skin wellness.

| | Baseline Skin Surface Moisture Reading | Post wear Skin Surface Moisture Reading | Change in Skin Surface Moisture Reading After Wear Time |
|---|---|---|---|
| Non breathable non-microporous film | 220 | 1,187 | 967 |
| 2,500 WVTR microporous film | 222 | 376 | 154 |
| 3,700 WVTR microporous film | 239 | 364 | 125 |

While various patents and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A method of making a monolithic film having regions of varied breathability comprising: providing a monolithic film wherein said monolithic film has a hydrohead of at least 50 mbars and a WVTR of at least 800 g/m$^2$/24 hours; selectively applying adhesive to a portion of said film thereby creating first and second regions within said monolithic film, said second region having dimensions of at least 3 cm by 3 cm and wherein the WVTR is decreased within said second region of said monolithic film relative to the WVTR of said first region.

2. The method of claim 1, wherein said monolithic film comprises a water-proof moisture-vapor permeable unitary sheet material comprising a monolithic polymeric matrix having continuous passages extending through the thickness of said matrix and opening into both surfaces thereof.

3. The method of claim 1, wherein said monolithic film comprises a multilayered coating from use in simultaneously imparting liquid resistance and breathability to a textile substrate wherein said coating comprising:

a first layer, adjacent to said textile substrate, consisting of a foamed adhesive wherein said adhesive is mechanically formed in solution from a fully reacted polymer latex chosen for the group consisting of polyvinyl chloride, acrylic, polyurethane, polyethylene, polystyrene copolymers of urethane and acrylic monomers, and mixtures thereof, to create an open celled surface;

a second layer, coated on said first layer distal to said textile substrate, comprising a monolithic membrane formed from a thermoplastic polymer selected from the group consisting of poly-vinyl diene fluoride, poly-vinyl diene chloride, and thermoplastic polyurethane, said second layer being capable of passing vapor across the width of said second layer in one direction from the surface adjacent to said first layer toward a third layer, and said second layer further being capable of inhibiting the flow of liquid across said second layer in the opposite direction; and, said third layer, coated on said second layer, to inhibit said flow of liquid in the direction of said second layer, and to impart abrasion resistance to said multilayered coating and said textile substrate, said third layer comprising a continuous film formed from latexes selected from the group consisting of acrylics, poly-vinyl chloride, polyurethane, and mixtures thereof.

4. The method of claim 1 wherein the application of adhesive decreases the WVTR of the second region by at least 25% and further wherein said second region has a minimum dimensions of 5 cm by 5 cm.

5. The method of claim 1 wherein the application of adhesive decreases the WVTR of the second region by at least 10% and further wherein said second region has a minimum dimensions of 5 cm by 5 cm.

6. The method of claim 4 wherein said second region comprises from about 5% to about 75% of the area of said monolithic film.

7. The method of claim 1 wherein said WVTR of said first region is at least about 3,000 and said WVTR of said second region is less than about 1,500.

8. The method of claim 6 wherein said thermoplastic polymer comprises a polyolefin polymer and wherein the basis weight of each of said first and second regions is below about 35g/m$^2$.

9. The method of claim 1 wherein said first region surrounds said second region.

10. The method of claim 1 wherein said first region partially surrounds said second region.

11. The method of claim 1 wherein said second region is continuous in the machine direction.

12. The method of claim 1 wherein said second region is discontinuous in the machine direction.

13. The method of claim 1 wherein said second region is continuous in the cross-machine direction.

14. The method of claim 1 wherein said second region is discontinuous in the cross-machine direction.

15. The method of claim 1 wherein said adhesive is selectively applied to said second region of said monolithic film in a coat layer.

16. The method of claim 15 wherein said second region comprises between about 5% and 75% of the area of said monolithic film and further wherein said first and second regions of said monolithic film each have a basis weight less than about 35g/m$^2$.

17. The method of claim 1 wherein said adhesive applied to said breathable film comprises a first WVTR and a second WVTR wherein first, second, and third regions are created within said monolithic film with said third region having a WVTR intermediate to the WVTR of said first and second regions.

18. The method of claim 16 wherein said second region comprises from about 5% to about 75% of said monolithic film.

19. The method of claim 17 wherein said second and third regions are continuous.

20. The method of claim 18 wherein said monolithic film has a WVTR gradient.

21. The method of claim 1 further comprising the step of laminating a nonwoven web to said monolithic film prior to applying said adhesive.

22. The method of claim 6 further comprising the step of laminating a nonwoven web to said monolithic film prior to applying said adhesive.

* * * * *